US006180557B1

(12) United States Patent
Choudhary et al.

(10) Patent No.: US 6,180,557 B1
(45) Date of Patent: Jan. 30, 2001

(54) SUPPORTED CATALYST USEFUL FOR FRIEDEL-CRAFTS REACTIONS AND PROCESS FOR THE PREPARATION OF ARALKYLATED AROMATIC COMPOUNDS USING THE CATALYST

(75) Inventors: Vasant Ramchandra Choudhary; Suman Kumar Jana; B-Phani Kiran, all of Maharashtra (IN)

(73) Assignee: Council of Scientific & Industrial Research, New Delhi (IN)

( * ) Notice: Under 35 U.S.C. 154(b), the term of this patent shall be extended for 0 days.

(21) Appl. No.: 09/209,834

(22) Filed: Dec. 11, 1998

(30) Foreign Application Priority Data

Aug. 13, 1998 (IN) .............................. 2388/DEL/98
Aug. 26, 1998 (IN) .............................. 2526/DEL/98

(51) Int. Cl.$^7$ ..................... B01J 27/06; B01J 27/125; B01J 27/128; B01J 27/135; B01J 27/138
(52) U.S. Cl. .................... 502/224; 502/226; 502/227; 502/229; 502/231
(58) Field of Search .................... 502/224, 226, 502/227, 229, 231

(56) References Cited

U.S. PATENT DOCUMENTS 5,106,800 * 4/1992 Moser et al. ............................ 502/53
5,128,300 * 7/1992 Chao et al. ............................ 502/227
5,858,908 * 1/1999 Bogdan et al. ....................... 502/227

* cited by examiner

Primary Examiner—Elizabeth D. Wood
(74) Attorney, Agent, or Firm—Michael D. Bednarek; Shaw Pittman

(57) ABSTRACT

A supported catalyst and a process for the preparation of the catalyst, the catalyst containing mixed metal oxides or halides deposited on porous catalyst carriers or supports, useful for heterogeneously or solid catalyzed Friedel-Crafts reactions such as alkylation, aralkylation, acylation, or aroylation of aromatic compounds in the preparation of fine chemicals. The supported catalyst has high activity for the Friedel-Crafts reactions when the aromatic ring activating groups are present in the aromatic ring to be aralkylated, acylated or aroylated, and also when the ring activating group is absent or when aromatic ring deactivating groups are present in the aromatic ring to aralkylated, acylated or aroylated, so that the reaction temperature is low and/or the time for completing the reaction is short. The catalyst can be separated and used repeatedly for catalytic reactions.

11 Claims, No Drawings

SUPPORTED CATALYST USEFUL FOR FRIEDEL-CRAFTS REACTIONS AND PROCESS FOR THE PREPARATION OF ARALKYLATED AROMATIC COMPOUNDS USING THE CATALYST

This invention relates to a novel supported catalyst useful for Friedel-Crafts reactions and process for the preparation of aralkylated aromatic compounds using the catalyst. This invention particularly relates to a novel supported catalyst, containing mixed metal oxides or halides deposited on porous catalyst carriers or supports useful for the heterogeneously or solid catalyzed Friedel-Crafts reactions, and a process for the preparation of the catalyst and also to a catalytic process for the preparation of aralkylated aromatic compounds by the aralkylation of aromatic compounds with aromatic aralkylating or alkylating agent, using the supported catalyst.

The catalyst preparation process of this invention could be used for the preparation of solid catalysts useful in the Friedel-Crafts reactions. The catalytic process for this invention could also be used for the preparation of aralkylated aromatic compounds, which are fine chemicals and/or intermediates used in the preparation of fine chemicals.

BACKGROUND OF THE INVENTION

A number of homogeneous and heterogeneous acidic catalysts useful for the Friedel-Crafts reactions, for examples alkylation, polyalkylation, aralkylation, acylation, aroylation and the like, are known in the prior art. Aralkylated aromatic compounds are useful fine chemicals and these are also used as intermediates in a member of organic syntheses. Both the homogeneous and heterogeneous catalysed liquid phase processes for the preparation of aralkylated aromatic compounds are known in the prior art, Homogeneous Catalysts for Friedel-Crafts Reactions The acylation and benzoylation of aromatic compounds and related Friedel-Crafts type reaction using homogeneous lewis acid catalysts are well-known in the prior art [ref G. A. Olah, in Friedel-Crafts and related reactions: vol. III, Acylation and related reactions, Wiley-Interscience Publ., New York, 1964].

A use of $CuCl_2$ as a homogeneous catalyst in the benzylation of benzene or substituted benzenes by benzyl chloride is disclosed in two U.S. patents, U.S. Pat. No. 3,678,122 (1972) and U.S. Pat. No. 3,679,760 (1972), A French patent, Fr. Demande 2,144,578 (1973), disclosed benzylation of p-substituted phenols by benzyl halides in the presence of homogeneous $ZnCl_2$ catalyst. A USSR patent, U.S.S.R. 394,353 (1973), disclosed a use Of $SnSO_4$ or $SnCl_2$ as homogeneous catalyst for the benzylation with benzyl chloride of m-dimethoxy benzene, A Japanese patent, Japan Kokai 7399,154 (1973), disclosed preparation of dibenzyl benzene derivatives by benzylation of benzene or substituted benzenes using $AlCl_3$, $FeCl_3$ and 98% $H_2SO_4$. A use of $H_2SO_4$ or $H_3PO_4$ and optionally 4-$CH_3C_6H_4SO_3H$, $ZnCl_2$, $BF_3$, etc. in the preparation of o-benzyltoluenes by the reaction of α o-chloromethyltoluene with a benzene derivative is disclosed in a German patent, Ger. Offen 2,456,747 (1976). A use of phosphoric acid and optionally $H_2SO_4$ or a Friedel-Crafts type metal halide in the benzylation of benzene with benzylether is disclosed in a U.S. patent, U.S. Pat. No. 4,049,733 (1977).

A German patent, Ger.offen 2,451,037 (1976), disclosed the use of HF as a catalyst for the benzoylation of aromatic compounds.

A French patent, Fr. Demande FR 2,496,097 (1982) disclosed the acylation of benzene by phthaleic anhydride using HF—$BF_3$ mixture.

More recently, an European Patent, Eur.Pat.Appl.FP 538, 704 (1993), disclosed a process for the preparation of p-substituted o-benzylphenols by treating phenols, p-R'$C_6H_4OH$ (R'=halo, alkyl, OH, alkoxy, alkylmercapto, aryl, aryloxy or arylmercapto), with Ar$CH_2X$ (Ar= corresponding aryl nucleus; X=halo, arylcarboxy, phenylsulfatoxy, hydroxy, alkoxy etc.) in a continuously functioning distillation apparatus in the presence of dissolved acid catalyst.

The main disadvantages of the use of homogeneous acid catalyst for the Friedel-Crafts processes are as follows:
1) The separation and recovery of the dissolved acid catalysts from the liquid reaction mixture is difficult.
2) The disposal of the used acid catalysts creates environmental pollution.
3) The homogeneous acid catalysts also pose several other problems such as high toxicity, corrosion, spent acid disposal and use of more than the stoichiometric amount.

Heterogeneous Catalysts for Friedel-Crafts Reactions

A German patent, Ger.Offen 2,547,030 (1977), disclosed the preparation of o-benzyltoluenes by the reaction of o-methylbenzyl halides with substituted benzenes in the presence of Al-silicate. The 2-$CH_3C_6H_4CH_2Cl$ was stirred with toltuene and Al-silicate (25%$Al_2O_3$) at 110° C. to give 81% 2-methylbenzyltoluene. According to a Japanese patent, Jpn. Kokai Tokkyo Koho JP 59,186,937 (1984), o-benzylphenol was prepared by the liquid phase reaction of benzyl alcohol with phenol in the presence of γ-$Al_2O_3$. For example 7.5 g γ-$Al_2O_3$ was added to a mixture of 32.5 g benzyl alcohol and 47 g phenol at 190° C. under stirring to give a product containing 49.9% o-benzylphenol. A German Patent, Ger. Offen DE 3,700,917 (1988), disclosed the preparation of p-substituted o-benzylphenols by benzylation of p-substituted phenols with benzylalcohol in the presence of Na—Y type zeolite. A mixture of 0.5 mole 4-$ClC_6H_4OH$, 0 1 mole $C_6H_5CH_2OH$ and 0,6 g of Na-Y type zeolite was heated at 200° C. for 3 hrs to give 25.4% 2-benzyl-4-chlorophenol.

A French patent, Fr. Demande FR 2,667,063 (1992), disclosed the preparation of 4-substituted benzophenones by aroylation of substituted benzenes by substituted benzoic acid in the presence of HY and Hβ type zeolites. Accordingly 4-$ClC_6H_4COOH$ and PhMe were heated 4 h at 200° C. under $2\times10^5$ Pa in the presence of calcined zeolite Hβ to give 84.4% 4-(4-$ClC_6H_4CO$) $C_6H_4Me$.

A recent paper by Vincent et al. (ref Tetrahedron Lett. 35, 1994, 2601), disclosed that H-ZSM-5 zeolite can catalyze the benzoylation by benzoyl chloride of phenol and anisole but not the benzoylation with benzoyl chloride of benzene, halobenzene and naphthalene, at 120° C. for 5 h.

A German patent, Ger. Offen DE 3,436,780 (1990), disclosed the process for the preparation of benzylbenzenes from benzenes and benzyl alcohols in the presence of activated bleaching earth and a diluent at 90–140° C. According to Japanese patent, Jpn Kokai Tokkyo Koho JP 03,170,442 (1991), benzylbiphenyls are manufactured by benzylating biphenyl and diphenylmethane with ≧1 compound from benzyl halides, benzyl alcohol, benzyl ether in the presence of a zeolite or silica-alumina catalyst. An European patent, Eur.Pat. appl. EP 428,081 (1991), disclosed a process of benylation of alkylbenzenes with benzyl chloride in the presence of H—Y or H—L zeolite catalyst. According to a German patent, Ger. Offen DE 4,038,933 (1992), disclosed a process for benzylation of aromatics using technical carbon catalysts.

Alkylation, aralkylation, acylation or aroylation of aromatic compound involves electrophilic substitution of H from the aromatic nucleus of the aromatic compound. It is well known in the prior art that the electrophilic substitution is favoured by the presence of electron donating groups, such as OH, alkyl, alkoxy, phenoxy, amine, alkyl amine, SH etc., in the aromatic compound. Whereas the electrophilic substitution is inhibited by the presence of electron withdrawing groups such as halo, nitro, cyano, carboxy, aldehyde, etc, in the aromatic compound, [ref, G. A. Olah, in Friedel-Crafts and related reactions, Wiley-Interscience Publ., New York, 1963].

Although some limitations of the homogeneous acid catalyzed processes are overcome in the prior art heterogeneous catalyzed processes described above, the alkylating, aralkylating, acylating or aroylating activity of the solid catalysts used in the prior art processes are low, particularly for alkylating, aralkylating, acylating or aroylating aromatic compounds containing electron withdrawing groups. Hence there is a great practical need for finding more efficient solid catalyst for the alkylating, aralkylating, acylating or aroylating of aromatic compounds. There is also a need for finding highly efficient solid catalyst also for the alkylating, aralkylating, acylating or aroylating of aromatic compounds containing electron withdrawing groups such as halo, nitro, cyano, carboxy, aldehyde, etc., Homogeneous Acid Catalysed Processes for Aralkylated Aromatic Compounds According to a U.S. patent, U.S. Pat. No. 3,678,122 (1972), diphenylmethane was prepared by treating a mixture of benzene and benzyl chloride with $CuCl_2$. A U.S. patent, U.S. Pat. No. 3,679,760 (1972), disclosed the preparation of diaryl alkanes by refluxing benzyl chloride, $C_6H_4R_1R_2$ (where $R_1$=H and $R_2$=H, $CH_3$ or OH) and $CuCl_2$.

A French patent, Fr. Demande 2,144,578 (1973), disclosed that substituted phenols p-$RC_6H_4OH$ (where R=halogen or $C_{1-4}$-alkyl) are benzylated by benzyl halides in the presence of $ZnCl_2$. A USSR patent, U.S.S.R. 394,353 (1973), disclosed preparation of 2,6- and 2,4-$(CH_3O)_2C_6H_3CH_2C_6H_5$ by treating m-$(CH_3O)_2C_6H_4$ with benzyl chloride in the presence of $SnSO_4$ catalyst at 145–150° C., or $SnCl_2$ catalyst at 165–170° C. A Japanese patent, Japan Kokai 7399,154 (1973), disclosed preparation of dibenzyl benzene derivatives by benzylation of benzene or substituted benzenes using Friedel-Crafts catalyst e.g., $AlCl_3$, $FeCl_3$ and 98% $H_2SO_4$. According to this patent, 200 g α-methyl benzyl chloride was added to a refluxing mixture of 500 g benzene and 5 g $AlCl_3$ and the whole mixture refluxed for 5 h to give 120 g α-methyl bezylbenzene.

According to a German patent, Ger. Offen 2,456,747 (1976), o-benzyltoluenes were prepared in ~90% yields by the reaction of α o-chloromethyltoluene with a benzene derivative in ≧1:7 ratio in the presence of $H_2SO_4$ and/or $H_3PO_4$ and optionally 4-$CH_3C_6H_4SO_3H$, $ZnCl_2$, $BF_3$, etc. Thus 135 parts 85% $H_3PO_4$, 270 parts 85% $H_2SO_4$, 10 parts 4-$CH_3C_6H_4SO_3H$, 70 parts $2CH_3C_6H_4CH_2Cl$ and 390 parts of $C_6H_6$ were heated at 75–80° C. for 4 h to give 89% 2-$CH_3C_6H_4CH_2C_6H_5$.

An U.S. patent U.S. Pat. No. 4,049,733 (1977), disclosed preparation of diphenylmethane by benzylation of benzene with benzylether using phosphoric acid and optionally $H_2SO_4$ or a Friedel-Crafts type metal halide.

European patent, Eup.Pat.Appl.EP 37,628 (1981), disclosed preparation of diphenylmethane by benzylation of benzene with chloromethylbenzenes in the presence of $H_2SO_4$ and a cationic surfactant or a non-ionic surfactant which is susceptible to protonation under strong acidic conditions.

A German patent, Ger.Offen DF 3,922,518 (1991), disclosed a process for the manufacture of α-methylbenzylphenol derivatives, which comprises the treatment of $C_{1-4}$-alkyl substituted phenols with styrene in the presence of phosphorus chloride catalyst. More recently, an European Patent, Eur.Pat.Appl.FP 538,704 (1993), disclosed a process for the preparation of p-substituted o-benzylphenols by treating phenols, p-$R'C_6H_4OH$ (R'= halo, alkyl, OH, alkoxy, alkylmercapto, aryl, aryloxy or arylmercapto), with $ArCH_2X$ (Ar=corresponding aryl nucleus; X=halo, arylcarboxy, phenylsulfatoxy, hydroxy, alkoxy etc.) in a continuously functioning distillation apparatus in the presence of dissolved acid catalyst.

The main disadvantages of the homogeneous acid catalyzed processes are as follows:
(i) The separation and recovery of the dissolved acid catalysts from the liquid reaction mixture is difficult.
(ii) The disposal of the used acid catalysts creates environmental pollution.
(iii) The homogeneous acid catalysts also pose several other problems such as high toxicity, corrosion, spent acid disposal and use of more than the stoichiometric amount.

Heterogeneous acid catalyzed processes for Aralkylated Aromatiuc Compounds

A German patent, Ger.Offen 2,547,0310 (1977), disclosed the preparation of o-benzyl-toluenes by the reaction of o-methylbenzyl halides with substituted benzenes in the presence of Al-silicate. The 2-$CH_3C_6H_4CH_2Cl$ was stirred with toluene and Al-silicate (25% $Al_2O_3$) at 110° C. to give 81% 2-methylbenzyltoluene. According to a Japanese patent, Jpn. Kokai Tokkyo Koho JP 59,186,937 (1984), o-benzylphenol was prepared by the liquid phase reaction of benzyl alcohol with phenol in the presence of γ-$Al_2O_3$. For example 7.5 g γ-$Al_2O_3$ was added to a mixture of 32.5 g benzyl alcohol and 47 g phenol at 190° C. under stirring to give a product containing 49.9% o-benzylphenol. A German patent, Ger. Offen DE 3,700,917 (1988), disclosed the preparation of p-substituted o-benzylphenols by benzylation of p-substituted phenols with benzylalcohol in the presence of Na—Y type zeolite. A mixture of 0.5 mole 4-$ClC_6H_4OH$, 0.1 mole $C_6H_5CH_2OH$ and 0.6 g of Na—Y type zeolite was heated at 200° C. for 3 hrs to give 25.4% 2-benzyl-4-chlorophenol.

A German patent, Ger. Offen DE 3,836,780 (1990), disclosed the process for the preparation of benzylbenzenes from benzenes and benzyl alcohols in the presence of activated bleaching earth and a diluent at 90–140° C. According to Japanese patent, Jpn Kokai Tokkyo Koho JP 03,170,442 (1991), benzylbiphenyls are manufactured by benzylating biphenyl and diphenylmethane with ≧1 compound from benzyl halides, benzyl alcohol, benzyl ether in the presence of a zeolite or silica-alumina catalyst. An European patent, Eur.Pat. appl. FP 428,081 (1991), disclosed a process of benzylation of alkylbenzenes with benzyl chloride in the presence of H—Y or H—L zeolite catalyst. According to a German patent, Ger. Offen DE 4,038,933 (1992), disclosed a process for benzylation of aromatics using technical carbon catalysts.

Aralkylation of aromatic compounds by aralkylating agent involves electrophilic substitution of H from the aromatic nucleus. It is well known in the prior art that the electrophilic substitution is favoured by the presence of electron donating groups, such as OH, alkyl, alkoxy, phenoxy, amine, alkyl amine, SH etc., in the aromatic compound to be aralkylated. Whereas in the absence of the electron donating groups, e.g. for benzene, naphthalene and anthracene, the aralkylation is relatively difficult [ref G. A. Olah, in Friedel-Crafts and related reactions, Wiley-Interscience Publ., New York, 1963].

Although some limitations of the homogeneous acid catalyzed processes are overcome by the prior art heterogeneous catalyzed processes described above, the aralkylating activity of the solid catalysts used in the above processes are low, particularly for aralkylating aromatic compounds not containing electron donating groups. Hence there is a great practical need for developing a process for the aralkylation of aromatic compounds with aralkylating agent, using more efficient, easily separable and reusable solid catalyst, There is also a need for developing a catalytic process for the aralkylation of aromatic compounds not containing electron donating groups, using highly efficient, easily separable and reusable solid catalyst.

This invention is made with the following objectives so that most of the drawbacks or limitations of the prior art homogeneous and heterogeneous catalyzed processes for the aralkylation of aromatic compounds could be overcome.

Accordingly, the main object of the present invention is to provide a novel supported catalyst comprising mixed metal oxides or halides, which has high activity for the Friedel-Crafts reactions not only when the aromatic ring activating groups (i.e. electron donating groups such as alkyl, hydroxy alkoxy, etc) are present in the aromatic ring to be aralkylated, acylated or aroylated but also when the ring activating group is absent or when aromatic ring deactivating groups (i.e. electron withdrawing groups such as halo, nitro, etc) are present in the aromatic ring to be aralkylated, acylated or aroylated, so that the reaction temperature is low and/or time for completing the reaction is short.and which can be used repeatedly for the catalytic rections, and also to provide an improved catalytic process for the preparation of aralkylated aromatic compound by the aralkylation of aromatic compound, with or without containing electron donating group, using the supported catalyst which is highly active supported solid catalyst comprising mixed metal oxides or halides deposited on micro-, meso- or macroporous catalyst carrier or support and has a high activity not only when the aromatic ring activating groups (i.e. electron donating groups such as alkyl, alkoxy, hydroxy, phenoxy, etc.) are present in the aromatic ring to be aralkylated but also when the ring activating group in the aromatic ring to be aralkylated is absent, so that the reaction temperature is low and/or time for completing the reaction is short.

Other important object of this invention is to provide a liquid phase process for the aralkylation of aromatic compounds using the novel supported solid catalyst which is easily separable and reusable in the process for several times.

Another important object of this invention is to provide a solid catalyzed liquid phase process for the aralkylating aromatic compounds even in the presence of moisture in the reaction mixture.

SUMMARY OF THE INVENTION

This invention provides a novel supported catalyst, useful for the Friedel-Crafts reactions, represented by a general formula:

$$A_aMZ_b(c)/S$$

wherein, A is selected from chemical elements Ga, Al, B, Zn, Fe, Sn, Ti, Th, Zr or a mixture of two or more thereof; M is selected from chemical elements In, Tl or a mixture thereof; Z is selected from chemical elements O, Cl, Br or I; S is porous catalyst support or carrier; a is A/M mole ratio in the range of about 0.001 to about 100; b is number of atoms of Z needed to fulfil the valence requirement of the metallic elements $A_aM$ present in the supported catalyst; c is weight percentage loading of $A_aMZ_b$ deposited on said catalyst support or carrier (S) in the range of about 0.5 wt % to about 50 wt %; and a process for the preparation of this catalyst, which comprises (i) depositing on said catalyst support mixed metal halides represented by formula:

$$A_aMD_d,$$

wherein A is selected from chemical elements Ga, Al, B, Zn, Fe, Sn, Ti, Th, Zr or a mixture of two or more thereof; M is selected from chemical elements In, Tl or a mixture thereof; D is chemical group selected from halogen Cl, Br or I or a mixture thereof; a is A/M mole ratio in the range of about 0.001 to about 100; and d is number of atoms of D needed to fulfil the valence requirement of the metallic elements A/M; from non-aqueous moisture-free solvent, in which said mixed metal halides are dissolved, by known catalyst impregnating techniques, such that the weight percent loading of said mixed metal halides on said catalyst support is in the range of about 0.5 wt % to about 50 wt %; or depositing on said catalyst support mixed metal compounds represented by formula:

$$A_aME_e,$$

wherein A is selected from chemical elements Ga, Al, B, Zn, Fe, Sn, Ti, Th, Zr or a mixture of two or more thereof; M is selected from chemical elements In, Tl or a mixture thereof; E is chemical group selected from O, $NO_3$, OH, halo, alkoxides or $C_nH_{2n+1}COO$, wherein n is in the range of 0 to 15; a is A/M mole ratio in the range of about 0,001 to about 100; e is number of groups of E needed to fulfil the valence requirement of the metallic elements $A_aM$; by known catalyst impregnation, coating or co-precipitation techniques, such that the weight percent loading of said catalyst support is in the range of about 0.5 wt % to about 50 wt %, (ii) heating the catalyst mass obtained from the step-i to dryness at a temperature of about 25° C. to about 250° C. under vacuum or in presence of air or inert gas, calcining the dried mass obtained from step-ii at a temperature of about 100° C. to about 700° C. under vacuum or in presence of air or inert gas for about 0.1 h to about 100 h, and also provides a catalytic process for the preparation of aralkylated aromatic compounds represented by a general chemical formula:

$$R_1R_2R_3R_4C_nH_{2n}C_6H_3R_5R_6,$$

by a liquid phase aralkylation of aromatic compounds, called substrates, represented by a general chemical formula:

$$R_1R_2R_3R_4M,$$

with aralkylating agents, represented by a general formula:

$$R_5R_6C_6H_3C_nH_{2n}X,$$

wherein is $C_6H_1$ or $C_{10}H_3$ or $C_{14}H_5$; M is $C_6H_2$ or $C_{10}H_4$ or $C_{14}H_6$; each of $R_1$, $R_2$, $R_3$ and $R_4$ groups is H or $C_nH_{2n+1}$ or $C_pH_{2p-1}$ or $C_6H_5$ or $C_nH_{2n}C_6H_5$ or OH or $OC_nH_{2n+1}$ or $OC_6H_5$ or halogen or $C_nH_{2n+1-x}Y_x$ or $NO_2$ or $NH_2$ or $NHC_nH_{2n+1}$ or $N(C_nH_{2n+1})_2$ or $NHCOC_nH_{2n+1}$ or $NHCOC_6H_5$ or CN or CHO or COOH or $COOC_nH_{2n+1}$ or $COC_nH_{2n+1}$ or $SO_3H$ or $SO_3C_nH_{2n+1}$ or SH or alkyl mercapto group or aryl mercapto group; each of $R_5$ and $R_6$ group is H or $CH_3$ or $C_2H_5$ or OH or $OCH_3$ or $OC_2H_5$ or $NO_2$ or halogen or $NH_2$; X is halogen or OH or $SO_3H$ or COOH or $OC_nH_{2n}C_6H_5$ or $OC_nH_{2n+1}$ or aryl carboxy group or alkyl carboxy group, x is an integer between 1 and 2n+1 and n & p are integers greater than or equal to 1 and 2, respectively, and C, H, N, O and S are chemical elements, using the above supported solid catalyst; the process comprises i) pretreating said solid catalyst at a temperature between 100° C. and 800° C. in a flow of moisture-free air or inert gas at a gas hourly space velocity in the range 1000–20000 $cm^3g^{-1}h^{-1}$ or under vacuum, for a period between 0.1 h and 10 h, ii) contacting a liquid mixture of aromatic compound and aralkylating agent having a mole ratio of aromatic compound to aralkylating agent between 0.1 and 100, in the absence or presence of a solvent, with said pretreated supported solid catalyst at a weight ratio of said catalyst to aralkylating agent between 0.02 and 2.0 in a stirred batch reactor in the presence of an inert gas bubbling through the reaction mixture and allowing the reaction to occur at a temperature between 25° C. and 300° C. at a pressure between 1 atm and 10 atm for a reaction period between 0.01 h and 50 h, iii) cooling the reaction mixture to a temperature about 25° C., removing said catalyst from the reaction mixture by filtration and then separating the reaction products from the reaction mixture by the known methods.

The main finding of this invention is that, the novel supported catalyst shows high activity in the aralkylation of aromatic compounds not only when the electron donating group, which is aromatic ring activating group, is present in the aromatic ring to be aralkylated but also when the electron donating group is absent in the aromatic ring to be aralkylated and hence the reaction temperature is low and/or the time required for completing the reaction is short.

Other important finding of this invention is that said solid catalyst can be separated easily and reused repeatedly in the process. Another important finding of this invention is that the aralkylation of aromatic compound over said catalyst occurs with high reaction rates even in the presence of moisture in the reaction mixture (i.e. a mixture of aromatic compound to be aralkylated, aralkylating agent, solid catalyst and solvent, if used). Yet another important finding of this invention is that the mechanism of the aralkylation of aromatic compounds over said solid catalyst is different from that of acid catalyzed Friedel-Crafts aralkylation reaction.

DETAILED DESCRIPTION OF THE INVENTION

Accordingly, this invention provides a novel supported catalyst, containing mixed metal oxides or halides deposited on porous catalyst carriers or supports, useful for the heterogeneously or solid catalyzed Friedel-Crafts reactions, a process for the preparation of the catalyst and also a catalytic process for the preparation of aralkylated aromatic compounds by the aralkylation of aromatic compounds with aromatic aralkylating or alkylating agent, using the novel supported catalyst.

The novel supported catalyst, useful for the Friedel-Crafts reactions of this invention is represented by a general formula:

$$A_aMZ_b(c)/S$$

wherein, A is selected from chemical elements Ga, Al, B, Zn, Fe, Sin, Ti, Th, Zr or a mixture of two or more thereof; M is selected from chemical elements In, Tl or a mixture thereof; Z is selected from chemical elements O, Cl, Br or I; S is porous catalyst support or carrier; a is A/M mole ratio in the range of about 0.001 to about 100; b is number of atoms of Z needed to fulfil the valence requirement of the metallic elements $A_aM$ present in the supported catalyst; c is weight percentage loading of $A_aMZ_b$ deposited on said catalyst support or carrier (S) in the range of about 0.5 wt % to about 50 wt %.

The process for the preparation of said novel catalyst of this invention comprises:

(i) depositing on said catalyst support mixed metal halides represented by formula:

$$A_aMD_d,$$

wherein A is selected from chemical elements Ga, Al, B, Zn, Fe, Sn, Ti, Th, Zr or a mixture of two or more thereof, M is selected from chemical elements In, Tl or a mixture thereof; D is chemical group selected from halogen Cl, Br or I or a mixture thereof, a is A/M mole ratio in the range of about 0.001 to about 100; and d is number of atoms of D needed to fulfil the valence requirement of the metallic elements $A_aM$; from non-aqueous moisture-free solvent, in which said mixed metal halides are dissolved, by known catalyst impregnating techniques, such that the weight percent loading of said mixed metal halides on said catalyst support is in the range of about 0.5 wt % to about 50 wt %; or depositing on said catalyst support mixed metal compounds represented by formula:

$$A_aME_e,$$

wherein A is selected from chemical elements Ga, Al, B, Zn, Fe, Sn, Ti, Th, Zr or a mixture of two or more thereof, M is selected from chemical elements In, Tl or a mixture thereof; E is chemical group selected from O, $NO_3$, OH, halo, alkoxides or $C_nH_{2n+1}COO$, wherein n is in the range of 0 to 15; a is A/M mole ratio in the range of about 0,001 to about 100; e is number of groups of E needed to fulfil the valence requirement of the metallic elements $A_aM$; by known catalyst impregnation, coating or co-precipitation techniques, such that the weight percent loading of said catalyst support is in the range of about 0.5 wt % to about 50 wt %, (ii) heating the catalyst mass obtained from the step-i to dryness at a temperature of about 25° C. to about 250° C. under vacuum or in presence of air or inert gas, calcining the dried mass obtained from step-ii at a temperature of about, 100° C. to about 700° C. under vacuum or in presence of air or inert gas for about 0.1 h to about 100 h;

In the catalyst preparation process of this invention, the porous catalyst carrier or support, S, is selected from micro- and/or meso porous zeolites and zeolite-like materials, synthetic and natural clays, silica gel, alumina and meso and/or macroporous catalyst carriers containing $SiO_2$, $Al_2O_3$, SiC, $ZrO_2$, $HfO_2$ or a mixture thereof, and more preferably, S is selected from mesoporous zeolites such as high silica MCM-41 and the like, silica gel, cation exchange clays such as montmorillonite clay and the like, and chemically inert or sintered low surface area macroporous catalyst carriers or supports containing $SiO_2$, $Al_2O_3$, SiC, $ZrO_2$, $HfO_2$ 1or a mixture thereof.

In the catalyst preparation process of this invention, a preferred loading of the active catalyst mass ($A_aMZ_b$, as described above) on the porous catalyst carrier or support (S), c, is from 2 wt % to 20 wt %, the preferred period of catalyst calcination in the step-iii of said catalyst preparation process is from 0.25 h to 25 h, the preferred chemical element A is Ga, Fe, Zn or a mixture thereof, and the preferred chemical element Z is O or Cl, The product obtained from the catalyst preparation process of this invention is a novel supported solid catalyst comprising of mixed metal oxides or halides deposited on porous catalyst carriers or supports, useful for the Fridel-Crafts reactions such as alkoylation, aralkylation d acylation or aroylation of aromatic compounds in the preparation of fine chemicals.

In the catalyst preparation process of this invention, said mixed metal oxides or halides ($A_aMZ_b$) are responsible for the catalytic activity and the main roles played by the porous catalyst carrier or support (S) are (i) to disperse the active catalyst components (said metal oxides or halides) uniformly and thereby increasing their surface area, (ii) to avoid sintering of said active catalyst components during the catalyst calcination, (iii) to provide high mechanical strength against crushing and/or abrasion to the catalyst during its use in the reaction and (iv) to ease the filtration of the catalyst from the reaction mixtures The said catalyst without catalyst carrier or support may be used for the Friedel-Crafts reactions but said catalyst with catalyst carrier or support is certainly more preferable.

In the catalyst preparation process of this invention, the presence of more than one metallic element in said active catalyst mass ($A_aMZ_b$) is essential for obtaining a synergetic effect, and thereby increasing the catalytic activity of said catalyst.

In the catalyst preparation process of this invention, said mixed metal compounds ($A_aME_e$) are catalyst precursors which are converted to mixed metal oxides directly by thermal decomposition or by hydrolysis or co-precipitation followed by calcination or decomposition at said calcination conditions.

In the catalyst preparation process of this invention, the non-aqueous solvent used for depositing said mixed metal halides ($A_aMD_d$) on said catalyst support may be selected from moisture-free volatile organic solvents such as acetonitrile, methanol, nitromethane, chloroform, and the like.

In the catalyst preparation process of this invention, said heating step (step-ii) is essential for drying or removing the solvent from the supported catalyst mass obtained in step-i and said calcining step (step-iii) is essential for decomposing said catalyst precursors to corresponding metal oxide or to disperse said mixed metal halides uniformly on the surface of said catalyst carrier or support.

Zeolites are crystalline aluminosilicates containing well defined channels or pores of uniform diameter. A large number of microporous zeolites, such as X, Y, mordenite, L, beta, ZSM-5, ZSM-8, ZSM-11, etc., and mesoporous zeolites, such as M41S type material, e.g. MCM-41, are known in the prior-art [ref Breck in Zeolite Molecular Sieves, Wiley-lnterscience Publ., New York, 1974; Beck and Co-workers. J.Am.Chem.Soc., vol. 14, page 10834,year 1992; Nature (London) vol.359, page 710, year 1992]. A number of cation exchange natural and synthetic clays having layered silicate stricture are known in the prior art [ref R. A. Schoonheydt "Clays: From two to three dimensions" in Studies in Surface Science and Catalysis, vol. 58, page 201–238, 1991; and K. Ohtsuka, Chem. Mater., vol. 9, page 2039–2051, year 19971.

In general, micropores have diameter below 1 nm; mesopores have diameter between about 1 nm and about 20 nm; and macropores have diameter above about 20 nm. Said catalyst containing only micropores of this process may be used in the Friedel-Crafts reactions when both the reactants of the reaction have critical size (minimum molecular diameter) less than 0.7 nm. Whereas said catalyst containing meso and/or macropores may be used in the said reactions for reactants having both small and large molecular size.

Said catalyst of this invention activates both the reactants of the Friedel-Crafts reactions and thereby shows high activity in the Friedel-Crafts reactions such as alkylation, aralkylation, acylation and aroylation reactions of aromatic compounds containing not only electron donating group, which activates the aromatic ring, but also in the absence of any electron donating group or even containing electron withdrawing group, which deactivates the aromatic ring.

The present invention reveals that the said supported solid catalysts containing mixed metal oxides or halides deposited on porous catalyst carrier or support, showing very high activity in the Friedel-Crafts reactions such as alkylation, aralkylation, acylation and aroylation reactions of aromatic compounds without containing any electron donating group or containing electron donating and/or electron withdrawing groups in their aromatic ring, can be prepared by the catalyst preparation process of this invention. Using these catalysts, the Friedel-Crafts reactions can be carried out at lower temperatures and/or in shorter reaction periods.

Accordingly, the present invention also provides a catalytic process for the preparation of aralkylated aromatic compounds represented by a general chemical formula:

$$R_1R_2R_3R_4QC_nH_{2n}C_6H_3R_5R_6,$$

by a liquid phase aralkylation of aromatic compounds, called substrates, represented by a general chemical formula:

$$R_1R_2R_3R_4M,$$

with aralkylating agents, represented by a general formula:

$$R_5R_6C_6H_3C_nH_{2n}X,$$

wherein is $C_6H_1$ or $C_{10}H_3$ or $C_{14}H_5$, M is $C_6H_2$ or $C_{10}H_4$ or $C_{14}H_6$; each of $R_1$, $R_2$, $R_3$ and $R_4$ groups is H or $C_nH_{2n+1}$ or $C_pH_{2p-1}$ or $C_6H_5$ or $C_nH_{2n}C_6H_5$ or OH or $OC_nH_{2n+1}$ or $OC_6H_5$ or halogen or $C_nH_{2n+1-x}Y_x$ or $NO_2$ or $NH_2$ or $NHC_nH_{2n+1}$ or $N(C_nH_{2n+1})_2$ or $NHCOC_nH_{2n+1}$ or $NHCOC_6H_5$ or CN or CHO or COOH or $COOC_nH_{2n+1}$ or $COC_nH_{2n+1}$ or $SO_3H$ or $SO_3C_nH_{2n+1}$ or SH or alkyl mercapto group or aryl mercapto group; each of $R_5$ and $R_6$ group is H or $CH_3$ or $C_2H_5$ or OH or $OCH_3$ or $OC_2H_5$ or $NO_2$ or halogen or $NH_2$; X is halogen or OH or $SO_3H$ or COOH or $OC_nH_{2n}C_6H_5$ or $OC_nH_{2n+1}$ or aryl carboxy group or alkyl carboxy group, x is an integer between 1 and 2n+1 and n & p are integers greater than or equal to 1 and 2, respectively, and C, H, N, O and S are chemical elements, using the said supported solid catalyst; the process comprises:

i) pretreating said solid catalyst at a temperature between 100° C. and 800° C. in a flow of moisture-free air or inert gas at a gas hourly space velocity in the range 1000–20000 $cm^3 g^{-1} h^{-1}$ or under vacuum, for a period between 0.1 h and 10 h, ii) contacting a liquid mixture of aromatic compound and aralkylating agent having a mole ratio of aromatic compound to aralkylating agent between 0.1 and 100, in the absence or presence of a solvent, with said pretreated supported solid catalyst at a weight ratio of said catalyst to aralkylating agent between 0.02 and 2,0 in a stirred batch reactor in the presence of an inert gas bubbling through the reaction mixture and allowing the reaction to occur at a temperature between 25° C. and 300° C. at a pressure between 1 atm and 10 atm for a reaction period between 0.01 h and 50 h, iii) cooling the reaction mixture to a temperature about 25° C., removing said catalyst from the reaction mixture by filtration and then separating the reaction products from the reaction mixture by the known methods.

Structural formula for said aralkylated aromatic compound represented by the chemical formula $R_1 R_2 R_3 R_4 Q C_n H_{2n} C_6 H_3 R_5 R_6$ is

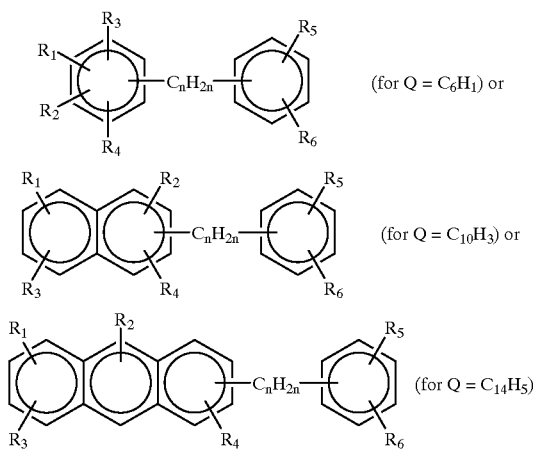

A structural formula for said aromatic compound represented by the chemical formula $R_1 R_2 R_3 R_4 M$ is

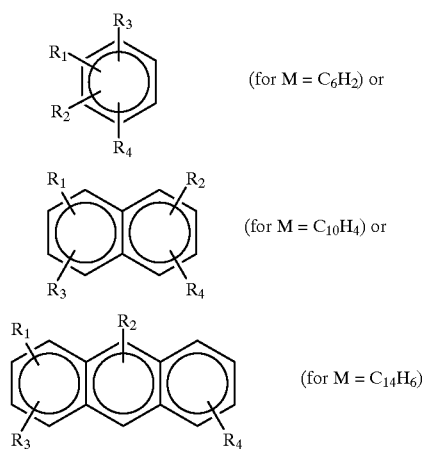

A structural formula for said aralkylating agent represented by the chemical formula $X C_n H_{2n} C_6 H_3 R_5 R_6$ is

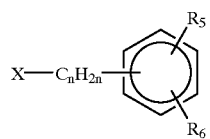

In the catalytic process of the present invention, the preferred reaction temperature may be between 40° C. and 200° C.; the preferred reaction pressure may be between 1 atm and 5 atm; the preferred reaction period may be between 0.05 h and 10 h; the preferred mole ratio of aromatic compound to aralkylating agent may be between 1 and 20; the preferred weight ratio of catalyst to aralkylating agent may be between 0.05 and 0.5; the preferred aromatic compound to be aralkylated may be benzene, higher aromatic hydrocarbon, hydroxy aromatic compound (e.g. phenols, naphthols, etc), alkoxy aromatic compound or phenoxy aromatic compound ($C_6 H_5 O C_6 H_5$, $C_{10} H_7 O C_6 H_5$, etc); and the preferred group in the aralkylating agent may be halogen or OH; the preferred chemical element, A, in said catalyst may be selected from Ga, Zn, Fe or a mixture of two or more thereof; the preferred chemical element, Z, in said catalyst is O or Cl; the preferred percentage loading of the active catalyst mass on catalyst carrier, c, in said catalyst may be in the range of about 2 wt % to about 20 wt %; and the preferred catalyst carrier or support, S, in the said catalyst may be selected from microporous silica gel, H-ZSM-5 or other pentasil (e g. H-ZSM-9, H-ZSM-11, etc.) zeolite, mesoporous MCM-41 zeolite, montmorillonite clay, and meso- and/or macroporous catalyst carrier containing $SiO_2$, $Al_2 O_3$, SiC, $ZrO_2$, $HfO_2$ or a mixture thereof.

Higher aromatic hydrocarbons may be aryl benzenes and alkyl or aryl polynuclear aromatic hydrocarbons.

The catalytic process of this invention can be carried out in a stirred batch reactor, fitted with a reflux condenser and arrangement for bubbling inert gas through the reaction mixture, known in the prior art for carrying out liquid phase reactions.

In the catalytic process of this invention, the main products formed are aralkylated aromatic compound and a by-product HX, wherein H=hydrogen and X=halogen or OH or $SO_3 H$ or COOH or $OC_n H_{2n} C_6 H_5$ or $OC_n H_{2n+1}$ or arylcarboxy group or alkylcarboxy group, depending upon said aralkylating agent used.

In the catalytic process of this invention, aromatic compound and aralkylating agent are reactants and are converted partially or completely to said products.

In the catalytic process of this invention, the role of said solvent, if used, is to dissolve solid reactant or reactants, to dilute reactants and/or to facilitate the reaction between aromatic compound and aralkylating agent. However, solvent may not be used in the process of this invention when both the reactants are liquid at said reaction conditions. Normally, said solvent is not converted in the process of this invention.

In the catalytic process of this invention, the role of inert gas bubbling continuously through the reaction mixture is to remove continuously said by-product from the reaction mixture so that the reverse reaction is avoided or minimised and the time required for completing the reaction is shortened.

In the catalytic process of this invention, the role of the reflux condenser fitted with the reactor is to condense reactants and solvents and to return them back to the reaction mixture and allow the inert gas, which is continuously bubbling through the reaction mixture, along with said by-product to escape from the reaction mixture.

In the catalytic process of this invention, the reaction pressure above atmospheric pressure may be used to allow the reaction to be carried out at temperature higher than the normal boiling point of the reactants and/or solvent, by increasing the boiling point of said reactants and/or solvent with increasing the reaction pressure.

Said catalyst, used in the catalytic process of this invention, is heterogeneous with respect to the reaction mixture and can be removed from the reaction mixture simply by filtration and the removed catalyst, after washing with solvent or said liquid aromatic compound, which is to be aralkylated, can be reused in the said process.

Said pretreatment to said catalyst in step-(i) of the catalytic process of present invention is necessary for removing moisture and other adsorbates adsorbed on the catalyst so that the catalyst shows its full efficiency for catalyzing the aralkylation reaction.

The role of said catalyst is to activate both the reactants, aromatic compound and aralkylating agent, The $R_1R_2C_6H_3C_nH_{2n}$ - - - X bond of said aralkylating agent is weakened by its interaction with the catalyst, leading to the formation of a stable carbocation $[R_1R_2C_6H_3C_nH_{2n}]^+$ (I) and $X^-$. In the presence of said carbocation (I), said aromatic compound is activated on the said catalyst by weakening its bond between aromatic nucleus and H, leading to the formation of a penta-coordinated carbocation by the combination of said activated aromatic compound and said carbocation (I). The said penta-coordinated carbocation is then decomposed to an aralkylated aromatic compound, the main product of the reaction, and a proton, which combines with $X^-$ to give HX, the by-product of the reaction.

Zeolites are crystalline aluminosilicates containing well defined channels or pores of uniform diameter. A large number of microporous zeolites, such as X, Y, mordenite, L, beta, ZSM-5, ZSM-8 ZSM-11, etc., and mesoporous zeolites, such as M41S type material, e.g. MCM-41, are known in the prior-art [ref Breck in Zeolite Molecular Sieves, Wiley-Interscience Publ., New York, 1974; Beck and Co-workers. J.Am.Chem.Soc., vol.114, page 10834,year 1992; Nature (London) vol.359, page 710, year 1992]. Montmorillonite is a natural clay having layered silicate structure and it is well known in the prior art [Ref R. A. Schoonheydt "Clays: from two to three dimensions" in Studies in Surface Science and Catalysis, vol. 58, page 201–238, 1991; and K. Ohtsuka, Chem. Mater,, 9 (1997) 2039–2051].

In general, micropores have diameter below 1 nm; mesopores have diameter between about 1 nm and about 20 nm; and macropores have diameter above about 20 nm. Said catalyst containing only micropores may be used in the process of this invention when both the reactants have minimum molecular diameter or critical size less than 0.7 nm. Whereas said catalyst containing meso and/or macropores may be used in the process of this invention for both small and large molecular size reactants.

By the process of this invention, benzene and anthracene can be benzylated with benzyl chloride to corresponding benzylated aromatic compounds with 100% conversion of benzyl chloride, at a temperature of 80° C. and 150° C., respectively and for a reaction period of 0.13 h and 0.3 h, respectively.

The present invention is described with respect to the following examples illustrating the process of this invention for the preparation of novel supported catalysts and also for the aralkylation of aromatic compounds using the novel supported solid catalysts. These examples are provided for illustrative purposes only and are not to be construed as limitations on the process of this invention.

Definition of terms used in the examples

Conversion of reactant (%)=mole % of the reactant converted to all products. All the ratios of aromatic compounds to aralkylating agent and of solvent to aralkylating agent are mole ratios. The solid catalyst to aralkylating agent ratio is weight ratio.

The flow rates of gases are measured at 0° C. and 1 atm pressure. Gas hourly space velocity (GHSV) is volume of gas, measured at 0° C. and 1 atm pressure, passed over unit mass of catalyst per hour.

Ac and Aa represent aromatic compound to be aralkylated and aralkylating agent, respectively.

The micropores, mesopores and macropores have pore diameter of below 1.0 nm, between about 1.0 nm and about 20 nm and above about 20 nm, respectively.

EXAMPLE-1

A supported catalyst: $Zn_{0.03}TlO_{0.53}$ (20.4 wt %)/SZ5564 was prepared by impregnating a mixture of 0.1 g zinc acetate and 5,0 g thallous acetate, dissolved in 14 ml distilled water, on 20 g fine particles (>100 mesh) of SZ5564 catalyst support [obtained from M/s. NORTON Co. U.S.A., main chemical composition=94.1% ($ZrO_2$+$HfO_2$), 3.5% CaO, 1.6% $SiO_2$ and 0.41% $Al_2O_3$; surface area=0.1 $m^2g^{-1}$; porosity=45%] by incipient wetness technique, drying the impregnated mass in an air oven at 110° C. for 10 h and calcining in air at 550° C. for 4 h. The surface area of the catalyst was 0.22 $m^2g^{-1}$. In the incipient wetness technique, the volume of impregnation solution is just sufficient to completely wet the solid to be impregnated and there is no free solution in the impregnation mixture.

EXAMPLE-2

A supported catalyst: $Fe_{17.2}TlCl_{54.6}$ (10 wt %)/Montmorrilonite K10 was prepared by impregnating a mixture of 0.9 g ferric chloride and 0.1 g thallic chloride, dissolved in 18 ml moisture-free acetonitrile, on 10 g Montmorillonite K10 clay (obtained from Aldrich Chemical Co. U.S.A.) by incipient wetness technique, drying the impregnated mass under vacuum at 40° C. for 20 h and then calcining or heating further in a flow of nitrogen free from oxygen and traces of moisture at 120° C. for 10 h.

EXAMPLE-3

A supported catalyst: $Ga_{12.6}InCl_{40.8}$ (11 wt %)/Montmorrilonite K10 was prepared by impregnating a mixture of 0.1 g indium chloride and 1.0 g gallium chloride, dissolved in 17 ml moisture-free methanol, on 10 g Montmorrilonite K10 clay (obtained from Aldrich Chemical Co. U.S.A.) by incipient wetness technique, drying the impregnated mass under vacuum at 100° C. for 1 h and then calcining or heating further in a flow of pure helium at 150° C. for 5 h.

EXAMPLE-4

A supported catalyst: $Ga_{10.0}InO_{16.5}$ (11.8 wt %)/SA5205 was prepared by impregnating a mixture of 2.8 g gallium nitrate and 0.33 g indium nitrate, dissolved in 7 ml distilled water, on 10 g SA5205 catalyst support, (obtained from M/s. NORTON Co. U.S.A.), having main chemical composition: 11.8% $SiO_2$, 86.1% $Al_2O_3$; surface area <0.01 $m^2g^{-1}$, pore volume=0.35 $cm^3g^{-1}$ and average pore diameter ~200 $\mu$m and particle size=100–150 mesh, by incipient wetness technique, drying the impregnated mass in an air oven at 100° C. for 15 h and calcining in air at 600° C. for 2 h. The surface area of the catalyst was 3.9 $m^2g^{-1}$.

EXAMPLE-5

A supported catalyst: $Ga_{11.0}InO_{18.0}$ (2.3 wt %)/MCM-41 was prepared by impregnating a mixture of 2.8 g gallium nitrate and 0.3 g indium nitrate, dissolved in 100 ml distilled water, on 50 g high silica meso-porous zeolite [prepared by the procedure described in the ref Choudhary et al., Proceeding of Indian Academy of Sciences, (Chemical Sciences) volume 109, page 229 and year 1997], by incipient wetness technique, drying the impregnated mass in an air oven at 100° C. for 20 h and calcining in air at 500° C. for 4 h. The surface area of the catalyst was 1102 $m^2g^{-1}$.

EXAMPLE-6

A supported catalyst: $Zn_{0.03}TlO_{0.53}$ (20.4 wt %)/SA5205 was prepared by impregnating a mixture of 0.3 g zinc nitrate and 5.0 g thallous nitrate, dissolved in 14 ml distilled water, on 20 g SA5205 catalyst support, described in EXAMPLE-4, by incipient wetness technique, drying the impregnated mass in an air oven at 120° C. for 8 h and calcining in air at 550° C. for 4 h. The surface area of the catalyst was ~0.1 $m^2g^{-1}$.

EXAMPLE-7

A supported catalyst: $Ga_{29.0}TlO_{44.0}$ (10.8 wt %)/$SiO_2$ gel was prepared by impregnating a mixture of 14.0 g gallium nitrate and 0.5 g thallous nitrate, dissolved in 50 ml distilled water, on 50 g $SiO_2$ gel catalyst support (Fuji Davison, A-type, surface area 720 $m^2g^{-1}$)in powdered form, by incipient wetness technique, drying the impregnated mass in an air oven at 125° C. for 6 h and calcining in air at 600° C. for 4 h. The surface area of the catalyst was 325 $m^2g^{-1}$.

EXAMPLE-8

A supported catalyst: $Ga_{0.05}TlO_{0.58}$ (5.1 wt %)/SA5205 was prepared by impregnating a mixture of 0.3 g gallium nitrate and 6.9 g thallous nitrate, dissolved in 70 ml distilled water, on 100 g SA5205 catalyst support, described in EXAMPLE-4, by incipient wetness technique, drying the impregnated mass in an air oven at 120° C. for 8 h and calcining in air at 550° C. for 4 h. The surface area of the catalyst was <0.1 $m^2g^{-1}$.

EXAMPLE-9

A supported catalyst: $Ga_{2.27}TlO_{3.9}$ (10 wt %)/SA5205 was prepared by impregnating a mixture of 2.05 g gallium nitrate and 0.94 g thallous nitrate, dissolved in 10 ml distilled water, on 15 g SA5205 catalyst support (obtained from M/s. NORTON Co. U.S.A.), having main chemical composition 11.8% $SiO_2$, 86.1% $Al_2O_3$; surface area <0.01 $m^2g^{-1}$, pore volume=0.35 $cm^3g^{-1}$ and average pore diameter ~200 μm and particle size=100–150 mesh, by incipient wetness technique, drying the impregnated mass in an air oven at 120° C. for 4 h and calcining at 500° C. in air for 4 h. The surface area of the catalyst was 3.1 $m^2g^{-1}$.

EXAMPLE-10

A supported catalyst: $Zn_{30}Ga_{1.0}Tl_{1.0}In_{0.5}O_{34}$ (113 wt %)/SA5205 was prepared by impregnating a mixture of 0.3 moles of zinc nitrate, 0.01 moles of gallium nitrate, 0.01 moles of thallic nitrate and 0.005 moles of indium nitrate, dissolved in 300 ml of distilled water, on 250 g SA5205 catalyst support, described in EXAMPLE-4, by wet impregnation technique, evaporating on water bath the excess solution while stirring, drying the impregnated mass in an air oven at 120° C. for 10 h and calcining in air at 500° C. for 4 h. The surface area of the catalyst was 0.3 $m^2g^{-1}$. In the wet impregnation technique, a more volume of impregnation solution than that required for completely wetting the solid to be impregnated is used and the excess of the solution is evaporated while stirring until there is no free solution is left in the impregnation mixture.

EXAMPLE-11

This example illustrates the process of this invention for the aralkylation of benzene, toluene, anisole and naphthalene by benzyl chloride or benzyl bromide to the corresponding benzylated aromatic compounds, using a $Zn_{0.03}TlO_{0.53}$ (20.4 wt %)/SZ5564 catalyst, prepared in Example-1.

The catalytic aralkylation reaction over the $Zn_{0.03}TlO_{0.53}$ (20.4 wt %)/SZ5564 was carried out by i) pretreating the catalyst in a quartz tubular reactor tinder a flow of moisture-free nitrogen at a gas hourly space velocity of 18,000 $cm^3g^{-1}h^{-1}$ at 500° C. for 1 h, and then ii) contacting said pretreated catalyst with 15 $cm^3$ liquid reaction mixture containing aromatic compound to be aralkylated and the aralkylating agent, benzyl chloride or benzyl bromide and optionally a solvent, n-heptane, in a stirred batch reactor (capacity: 50 $cm^3$) fitted with a reflux condenser, mercury thermometer dipped in the reaction mixture and an inlet tube for passing gas through the reaction mixture, under vigorous stirring, while bubbling moisture-free $N_2$ gas through the reaction mixture at the reaction conditions given in TABLE-1 and following the course of the reaction by measuring quantitatively the HCl or HBr evolved during the reaction by absorbing it in aqueous NaOH solution by a simple acid-base titration using phenolphthalein indicator, and iii) cooling the reaction mixture to room temperature (25° C.) and analysing the products and unconverted reactants present in the reaction mixture, after separating the solid catalyst from it by filtration, using chromatographic technique. The results are included in TABLE-1.

TABLE 1

Reaction conditions and results of the aralkylation of different aromatic compounds over the $Zn_{0.03}TlO_{0.53}$(20.4 wt %) SZ5564 catalyst

| Reactants: | | | | |
|---|---|---|---|---|
| Aromatic compound (Ac) | $C_6H_6$ | $C_6H_5CH_3$ | $C_6H_5OCH_3$ | $C_{10}H_8$ |
|  | (benzene) | (toluene) | (anisole) | (naphthalene) |
| Aralkylating agent (Aa) | $C_6H_5CH_2Cl$ | $C_6H_5CH_2Br$ | $C_6H_5CH_2Cl$ | $C_6H_5CH_2Cl$ |
| Reaction Conditions: | | | | |
| Solvent | Nil | nil | Nil | n-octane |
| Ac/Aa mole ratio | 17.0 | 17.0 | 17.0 | 1.4 |

TABLE 1-continued

Reaction conditions and results of the aralkylation of different aromatic compounds over the $Zn_{0.03}TIO_{0.53}$(20.4 wt %) SZ5564 catalyst

| Reactants: | | | | |
|---|---|---|---|---|
| Aromatic compound (Ac) | $C_6H_6$ (benzene) | $C_6H_5CH_3$ (toluene) | $C_6H_5OCH_3$ (anisole) | $C_{10}H_8$ (naphthalene) |
| Aralkylating agent (Aa) | $C_6H_5CH_2Cl$ | $C_6H_5CH_2Br$ | $C_6H_5CH_2Cl$ | $C_6H_5CH_2Cl$ |
| Solvent/Aa mole ratio | 0.0 | 0.0 | 0.0 | 9.0 |
| Catalyst/Aa weight ratio | 0.1 | 0.1 | 0.1 | 0.1 |
| Temperature (° C.) | 80.0 | 40.0 | 80.0 | 80.0 |
| Pressure (atm) | 1.0 | 1.0 | 1.0 | 1.0 |
| $N_2$ flow ($cm^3 min^{-1}$) | 30.0 | 30.0 | 30.0 | 30.0 |
| Reaction time (h) | 0.13 | 19.5 | 0.12 | 0.60 |
| Conversion of aralkylating agent (%) | 100.0 | 100.0 | 100.0 | 51.0 |
| Main product of reaction | $C_6H_5CH_2C_6H_5$ (diphenylmethane) | $CH_3C_6H_4CH_2C_6H_5$ (benzyl toluene) | $CH_3OC_6H_4CH_2C_6H_5$ (benzyl anisole) | $C_{10}H_7CH_2C_6H_5$ (benzyl naphthalene) |
| By-product of reaction | HCl | HBr | HCl | HCl |

Ac = Aromatic compound, Aa = Aralkylating agent

EXAMPLE-12

This example illustrates the process of this invention for the aralkylation of benzene and higher aromatic hydrocarbons by benzyl chloride, benzyl alcohol or $C_6H_5C_4H_8Cl$, as an aralkylating agent, to corresponding aralkylated aromatic compounds, using $Ga_{10.0}InO_{16.5}$ (11 8 wt %)/SA5205 catalyst, prepared in Example-4.

The catalytic aralkylation of benzene and higher aromatic hydrocarbons by benzyl chloride, benzyl alcohol or $C_6H_5C_4H_8Cl$, over the $Ga_{10.0}InO_{16.5}$ (11.8 wt %)/SA5205 catalyst was carried out by the procedure same as that described in EXAMPLE-11 at the reaction conditions given in TABLE-2. The results are included in TABLE-2.

TABLE 2

Reaction conditions and results of the aralkylation of different aromatic compounds over the $Ga_{10.0}InO_{16.5}$(11.8 wt %)/SA 5205 catalyst.

| Reactants: | | | | |
|---|---|---|---|---|
| Aromatic compound (Ac) | $C_6H_6$ (benzene) | $C_6H_5CH_3$ (toluene) | $C_{14}H_{10}$ (anisole) | $p-C_6H_4(CH_3)_2$ (naphthalene) |
| Aralkylating agent (Aa) | $C_6H_5CH_2Cl$ | $C_6H_5CH_2Br$ | $C_6H_5CH_2Cl$ | $C_6H_5CH_2Cl$ |
| Reaction Conditions: | | | | |
| Solvent | nil | nil | n-heptane | Nil |
| Ac/Aa mole ratio | 17.0 | 17.0 | 1.1 | 17.0 |
| Solvent/Aa mole ratio | 0.0 | 0.0 | 12.0 | 0.0 |
| Catalyst/Aa weight ratio | 0.1 | 0.1 | 0.1 | 0.1 |
| Temperature (° C.) | 80.0 | 110.0 | 150.0 | 80.0 |
| Pressure (atm) | 1.0 | 1.0 | 5.0 | 1.0 |
| $N_2$ flow ($cm^3 min^{-1}$) | 30.0 | 30.0 | 30.0 | 50.0 |
| Reaction time (h) | 1.0 | 5.0 | 0.3 | 0.25 |
| Conversion of aralkylating agent (%) | 100 | 100 | 100 | 100 |
| Main product of reaction | $C_6H_5CH_2C_6H_5$ (diphenyl butane) | $CH_3C_6H_4CH_2C_6H_5$ benzyl toluene) | $CH_3OC_6H_4CH_2C_6H_5$ (benzyl anthracene) | $C_{10}H_7CH_2C_6H_5$ (benzyl p-xylene) |
| By-product of reaction | HCl | $H_2O$ | HCl | HBr |

Ac = Aromatic compound, Aa = Aralkylating agent

EXAMPLE 13

This example illustrates the process of this invention for the aralkylation of benzene, higher aromatic hydrocarbon, anisole and phenol by benzyl chloride in the presence or absence of any solvent, over $Ga_{12.6}InCl_{40.8}$ (11.0 wt %)/Montmorillonite K10 catalyst, prepared in Example-3.

The catalytic aralkylation reactions over the catalyst was carried out by the procedure same as that described in EXAMPLE-11 at the reaction conditions given in TABLES-3 and 4, except that the catalyst pre-treatment was carried out under vacuum (2 torr pressure) at 100° C. for 10 h. The results are included in TABLES-3 and 4.

TABLE 3

Reaction conditions and results of the aralkylation of different aromatic compounds over the $Ga_{12.6}InCl_{40.8}$ (11.0 wt %)/Montmorillonite K10 catalyst.

| Reactants: | | | |
|---|---|---|---|
| Aromatic compound (Ac) | $C_6H_6$ (benzene) | $C_6H_5CH_3$ (anisole) | $C_{14}H_{10}$ (phenol) |
| Aralkylating agent (Aa) | $C_6H_5CH_2Cl$ | $C_6H_5CH_2Br$ | $C_6H_5CH_2Cl$ |
| Reaction Conditions: | | | |
| Solvent | nil | nil | n-octane |
| Ac/Aa mole ratio | 17.0 | 17.0 | 1.0 |
| Solvent/Aa mole ratio | 0.0 | 0.0 | 9.4 |
| Catalyst/Aa weight ratio | 0.1 | 0.1 | 0.1 |
| Temperature (° C.) | 80.0 | 80.0 | 80.0 |
| Pressure (atm) | 1.0 | 1.0 | 1.0 |
| $N_2$ flow ($cm^3 min^{-1}$) | 30.0 | 30.0 | 30.0 |
| Reaction time (h) | 0.25 | 3.0 | 3.3 |
| Conversion of aralkylating agent (%) | 96 | 100 | 100 |
| Main product of reaction | $C_6H_5CH_2C_6H_5$ (diphenylmethane) | $CH_3OC_6H_4CH_2C_6H_5$ (benzylanisole) | $HOC_6H_4CH_2C_6H_5$ (benzylphenol) |
| By-product of reaction | HCl | HCl | HCl |

Ac = Aromatic compound, Aa = Aralkylating agent

TABLE 4

Reaction conditions and results of the aralkylation of different aromatic compounds over the $Ga_{12.6}InCl_{40.8}$ (11.0 wt %)/Montmorillonite K10 catalyst.

| Reactants: | | | |
|---|---|---|---|
| Aromatic compound (Ac) | $(CH_3)_2C_6H_4$ (p-xylene) | $(CH_3)_3C_6H_3$ (mesitylene) | $CH_3C_6H_5$ (toluene) |
| Aralkylating agent (Aa) | $C_6H_5CH_2Cl$ | $C_6H_5CH_2Br$ | $C_6H_5CH_2Cl$ |
| Reaction Conditions: | | | |
| Solvent | nil | nil | nil |
| Ac/Aa mole ratio | 17.0 | 20.0 | 5.0 |
| Solvent/Aa mole ratio | 0.0 | 0.0 | 0.0 |
| Catalyst/Aa weight ratio | 0.1 | 0.1 | 0.1 |
| Temperature (° C.) | 80.0 | 80.0 | 70.0 |
| Pressure (atm) | 1.0 | 1.0 | 1.0 |
| $N_2$ flow ($cm^3 min^{-1}$) | 40.0 | 40.0 | 30.0 |
| Reaction time (h) | 0.6 | 1.0 | 0.5 |
| Conversion of aralkylating agent (%) | 100 | 100 | 100 |
| Main product of reaction | $(CH_3)_2C_6H_3CH_2C_6H_5$ (benzyl p-xylene) | $(CH_3)_3C_6H_2CH_2C_6H_5$ (benzyl mesitylene) | $CH_3C_6H_4CH_2C_6H_5$ (benzyl toluene) |

TABLE 4-continued

Reaction conditions and results of the aralkylation of different aromatic compounds over the $Ga_{12.6}InCl_{40.8}$ (11.0 wt %)/Montmorillonite K10 catalyst.

Reactants:

| Aromatic compound (Ac) | $(CH_3)_2C_6H_4$ (p-xylene) | $(CH_3)_3C_6H_3$ (mesitylene) | $CH_3C_6H_5$ (toluene) |
|---|---|---|---|
| Aralkylating agent (Aa) | $C_6H_5CH_2Cl$ | $C_6H_5CH_2Br$ | $C_6H_5CH_2Cl$ |
| By-product of reaction | HCl | HCl | HCl |

Ac = Aromatic compound, Aa = Aralkylating agent

EXAMPLE-14

This example illustrates the process of this invention for the aralkylation of benzene, toluene and anisole by benzyl bromide, using $Ga_{11.0}InO_{18.0}$ (2.3 wt %)/MCM-41 catalyst., prepared in Example-5.

The catalytic aralkylation reaction over the catalyst was carried out by the procedure same as that described in EXAMPLE-11 at the reaction conditions given in TABLE-5, except that in the present case the pretreatment of the catalyst was carried out in the flow of moisture-free $N_2$ at 700° C. at a gas hourly space velocity of 3000 $cm^3g^{-1}h^{-1}$ for 0.5 h. The results are included in TARILE-5.

chloride to corresponding aralkylated aromatic hydrocarbons, using $Fe_{0.01}Ga_{0.1}InO_{1.665}$ (20 wt %)/MCM-4]catalyst.

The $Fe_{0.01}Ga_{0.1}InO_{1.665}$ (20 wt %)/MCM-41catalyst was prepared by depositing a mixture of 21.7 g indium nitrate, 1.84 g gallium nitrate and 0.3 g ferric nitrate from their aqueous solution on 50 g high silica MCM-41, prepared by the process described earlier [ref Choudhary et al. Proc. Ind. Acad. Sci. (Chemical Sciences), 109 (1997) 229], by incipient wetness impregnation technique, drying the impregnated mass at 110° C. for 10 h and then calcining in an air oven at 550° C. for 4h.

TABLE 5

Reaction conditions and results of the aralkylation of benzene and toluene and anisole over the $Ga_{11.0}InO_{18.0}$ (2.3 wt %)/MCM-41 catalyst.

Reactants:

| Aromatic compound (Ac) | $C_6H_6$ (benzene) | $CH_3C_6H_5$ (toluene) | $C_6H_5OCH_3$ (anisole) |
|---|---|---|---|
| Aralkylating agent (Aa) | $C_6H_5CH_2Br$ | $C_6H_5CH_2Br$ | $C_6H_5CH_2Br$ |
| Reaction Conditions: | | | |
| Solvent | nil | Nil | nil |
| Ac/Aa mole ratio | 17.0 | 17.0 | 17.0 |
| Solvent/Aa mole ratio | 0.0 | 0.0 | 0.0 |
| Catalyst/Aa weight ratio | 0.1 | 0.1 | 0.1 |
| Temperature (° C.) | 80.0 | 80.0 | 80.0 |
| Pressure (atm) | 1.0 | 1.0 | 1.0 |
| $N_2$ flow ($cm^3min^{-1}$) | 30.0 | 30.0 | 30.0 |
| Reaction time (h) | 5.0 | 5.0 | 5.0 |
| Conversion of aralkylating agent (%) | 100 | 100 | 100 |
| Main product of reaction | $C_6H_5CH_2C_6H_5$ (benzylbenzene) | $CH_3C_6H_4CH_2C_6H_5$ (benzyltoluene) | $CH_3OC_6H_4CH_2C_6H_5$ (benzylanisole) |
| By-product of reaction | HBr | HBr | HBr |

Ac = Aromatic compound, Aa = Aralkylating agent

EXAMPLE-15

This example illustrates the process of this invention for the aralkylation of benzene and methyl benzenes by benzyl The catalytic aralkylation of benzene and methyl benzenes by benzyl chloride over the above catalyst has been carried out by the procedure same as that described in EXAMPLE-11, at the reaction conditions given in TABLE-6. The results are presented in TABLE-6.

TABLE 6

Reaction conditions and results of the aralkylation of benzene, p-xylene and mesitylene over the $Fe_{0.01}Ga_{0.11}nO_{1.665}$ (20 wt %)/MCM-41 catalyst.

Reactants:

| | | | |
|---|---|---|---|
| Aromatic compound (Ac) | $C_6H_6$ (benzene) | $(CH_3)_2C_6H_4$ (p-xylene) | $(CH_3)_3C_6H_3$ (mesitylene) |
| Aralkylating agent (Aa) | $C_6H_5CH_2Cl$ | $C_6H_5CH_2Cl$ | $C_6H_5CH_2Cl$ |

Reaction Conditions:

| | | | |
|---|---|---|---|
| Solvent | nil | nil | Nil |
| Ac/Aa mole ratio | 17.0 | 17.0 | 17.0 |
| Solvent/Aa mole ratio | 0.0 | 0.0 | 0.0 |
| Catalyst/Aa weight ratio | 0.1 | 0.1 | 0.1 |
| Temperature (° C.) | 80 | 135 | 162 |
| Pressure (atm) | 1.0 | 1.0 | 1.0 |
| $N_2$ flow ($cm^3 min^{-1}$) | 30.0 | 30.0 | 30.0 |
| Reaction time (h) | 0.3 | 0.25 | 0.25 |
| Conversion of aralkylating agent (%) | 100 | 100 | 100 |
| Main product of reaction | $C_6H_5CH_2C_6H_5$ (diphenylmethane) | $(CH_3)_2C_6H_3CH_2C_6H_5$ (benzyl p-xylene) | $(CH_3)_3C_6H_2CH_2C_6H_5$ (benzyl mesitylene) |
| By-product of reaction | HCl | HCl | HCl |

Ac = Aromatic compound, Aa = Aralkylating agent

EXAMPLE-16

This example illustrates the process of this invention for the aralkylation of benzene, toluene and anisole by benzyl chloride, using $Zn_{1.0}Ga_{2.0}InO_{5.5}$ (5 wt %)/HZSM-5 catalyst.

The $Zn_{1.0}Ga_{2.0}InO_{5.5}$ (5 wt %)/HZSM-5 catalyst was prepared by depositing a mixture of 2.22 g zinc nitrate, 7.64 g gallium nitrate and 4.5 g indium nitrate from their aquous solution on 100 g HZSM-5, having Si/Al ratio of 35.0, degree of $H^+$exchange >99% and crystal size of 3–5 μm, by incipient weiness inpregnation technique, drying the inpregnated mass at 100° C. for 16 h and then calcining in an air oven at 550° C. for 4 h.

The aralkylation reactions were carried out using the above catalyst, by the procedure same as that described in EXAMPLE-11, except that the period of catalyst pretreatment was 0.2 h, at the reaction conditions given in TABLE-7.

TABLE 7

Reaction conditions and results of tbe aralkylation of benzene, tolune and anisole over the $Zn_{1.0}Ga_{2.0}InO_{5.5}$ (5 wt %)/HZSM-5 catalyst.

Reactants:

| | | | |
|---|---|---|---|
| Aromatic compound (Ac) | $C_6H_6$ (benzene) | $CH_3C_6H_5$ (toluene) | $CH_3OC_6H_5$ (anisole) |
| Aralkylating agent (Aa) | $C_6H_5CH_2Cl$ | $C_6H_5CH_2Cl$ | $C_6H_5CH_2Cl$ |

Reaction Conditions:

| | | | |
|---|---|---|---|
| Solvent | nil | Nil | Nil |
| Ac/Aa mole ratio | 17.0 | 17.0 | 17.0 |
| Solvent/Aa mole ratio | 0.0 | 0.0 | 0.0 |
| Catalyst/Aa weight ratio | 0.1 | 0.1 | 0.1 |
| Temperature (° C.) | 80.0 | 80.0 | 100.0 |
| Pressure (atm) | 1.0 | 1.0 | 1.0 |
| $N_2$ flow ($cm^3 min^{-1}$) | 30.0 | 40.0 | 40.0 |
| Reaction time (h) | 0.5 | 0.5 | 0.5 |
| Conversion of aralkylating agent (%) | 100 | 100 | 100 |
| Main product of reaction | $C_6H_5CH_2C_6H_5$ (diphenyhmethane) | $CH_3C_6H_4CH_2C_6H_5$ (benzyltoluene) | $CH_3OC_6H_4CH_2C_6H_5$ (benzyl anisole) |

TABLE 7-continued

Reaction conditions and results of the aralkylation of benzene, tolune and anisole over the $Zn_{1.0}Ga_{2.0}InO_{5.5}$ (5 wt %)/HZSM-5 catalyst.

| Reactants: | | | |
|---|---|---|---|
| Aromatic compound (Ac) | $C_6H_6$ (benzene) | $CH_3C_6H_5$ (toluene) | $CH_3OC_6H_5$ (anisole) |
| Aralkylating agent (Aa) | $C_6H_5CH_2Cl$ | $C_6H_5CH_2Cl$ | $C_6H_5CH_2Cl$ |
| By-product of reaction | HCl | HCl | HCl |

Ac = Aromatic compound, Aa = Aralkylating agent

EXAMPLE-17

This example illustrates the process of this invention for the aralkylation of benzene by benzyl chloride using a $Ga_{0.05}InO_{1.575}$ (20 wt %)/SA5205 catalyst even when the moisture is present in the reaction mixture and also reusing the catalyst number of times for subsequent batches of the aralkylation of benzene.

The $Ga_{0.05}InO_{1.575}$ (20 wt %)/SA5205 catalyst was prepared by depositing a mixture of 0.092 g gallium nitrate and 2.17 g indium nitrate from their aquous solution on 5 g macroporous SA5205 catalyst carrier, by incipient wetness impregnation technique, drying the impregnated mass at 120° C. for 4 h and then calcining in an air oven at 600° C. for 2 h.

The aralkylation of benzene by benzyl chloride over the above catalyst was carried out by the procedure same as that described in EXAMPLE-11, except that in the present case the reaction was carried out using dry (moisture-free benzene) or wet benzene (benzene saturated with water) and also the catalyst used in the second and subsequent batches was obtained by filtration from the reaction mixture of the previous batch, at the reaction conditions given in TABLE-8. Before reusing the filtered catalyst, it was washed with benzene. The results are presented in TABLE-8.

The results (TABLE-8) show that the catalyst of this invention catalyses the aralkylation reaction even when water or moisture is present in the reaction mixture and also the catalyst can be reused repeatedly in the process of this invention, even for aralkylating moisture containing benzene.

TABLE 8

Reaction conditions and results of the aralkylation of benzene, with or without containing moisture, by benzyl chloride over the $Ga_{0.05}InO_{1.575}$ (20 wt %)/SA5205 catalyst.

| Batch No. | 1 | 2 | 3 | 4 |
|---|---|---|---|---|
| Catalyst used | Fresh $Ga_{0.05}InO_{1.575}$ (20 wt %)/SA5205 Catalyst | Obtained after batch no. 1 by filtration and washing with benzene | Obtained after batch no. 1 by filtration washing with benzene | Obtained after batch no. 1 by filtration and washing with benzene |
| Reactants: | | | | |
| Aromatic compound (Ac) | Dry benzene | Benzene saturated with water | Benzene saturated with water | Benzene saturated with water |
| Aralkylating agent (Aa) | $C_6H_5CH_2Cl$ | $C_6H_5CH_2Cl$ | $C_6H_5CH_2Cl$ | $C_6H_5CH_2Cl$ |
| Reaction Conditions: | | | | |
| Solvent | nil | nil | Nil | nil |
| Ac/Aa mole ratio | 17.0 | 17.0 | 17.0 | 17.0 |
| Solvent/Aa mole ratio | 0.0 | 0.0 | 0.0 | 0.0 |
| Catalyst/Aa weight ratio | 0.1 | 0.1 | 0.1 | 0.1 |
| Temperature (° C.) | 80.0 | 80.0 | 80.0 | 80.0 |
| Pressure (atm) | 1.0 | 1.0 | 1.0 | 1.0 |
| $N_2$ flow ($cm^3 min^{-1}$) | 40.0 | 40.0 | 40.0 | 40.0 |
| Reaction time (h) | 0.75 | 0.75 | 0.75 | 0.75 |
| Conversion of aralkylating agent (%) | 100 | 100 | 100 | 100 |
| Main product of reaction | $C_6H_5CH_2C_6H_5$ (diphenylmethane) | $C_6H_5CH_2C_6H_5$ (diphenylmethane) | $C_6H_5CH_2C_6H_5$ (diphenylmethane) | $C_6H_5CH_2C_6H_5$ (diphenyymethane) |

TABLE 8-continued

Reaction conditions and results of the aralkylation of benzene, with or without containing moisture, by benzyl chloride over the $Ga_{0.05}InO_{1.575}$ (20 wt %)/SA5205 catalyst.

| Batch No. | 1 | 2 | 3 | 4 |
|---|---|---|---|---|
| By-product of reaction | HCl | HCl | HCl | HCl |

Ac = Aromatic compound, Aa = Aralkylating agent

The main advantages of the supported catalysts of this invention over the prior art catalysts useful for the Friedel-Crafts reactions are as follows:

1. The supported catalysts of this invention has a number of advantages over the earlier homogeneous catalysts used for the Friedel-Crafts reactions, as follows:

According to this invention
   i) the catalyst used for the Friedel-Crafts reaction is heterogeneous solid catalyst and hence it can be separated from the reaction products simply by filtration, and moreover since the catalysts are supported ones, their filtration is easier,
   ii) the separated catalysts can be reused in the process for a number of times, and
   iii) also the catalysts are non corrosive, therefore most of the serious problems associated with homogeneous catalyst used in the earlier homogeneous catalysed Friedel-Crafts reactions are overcome by the supported solid catalysts of this invention.

2, The catalysts of this invention have also number of advantages over the prior art solid catalysts used for the Friedel-Crafts reactions, as follows:
   i) The activity of the catalysts of this invention in the Friedel-Crafts reactions is higher.
   ii) The catalysts of the present invention can be used for the Friedel-Crafts reactions involving reactants of any molecular size i.e. for both small and big reactant molucules.
   iii) By using the catalysts of this invention, the Friedel-Crafts reactions can be carried out at mild reaction conditions even though when the aromatic compound does not contain any aromatic nucleus activating group or electron donating group, for example when aromatic compound is benzene, or also when the aromatic compound contains electron withdrawing group, such as halide, which has highly deactivating effect on the aromatic nucleus for the alkylation, aralkylation, acylation or aroylation reaction.

The main advantages of the catalytic process of this invention over the prior art processes for the aralkylation of aromatic compound are as follows:

1) The process of this invention has a number of advantages over the earlier homogeneous catalyzed processes for the preparation of aralkylated aromatic compounds, as follows:
In the process of this invention,
   i) the catalyst used is heterogeneous solid catalyst and hence it can be separated from the reaction products simply by filtration,
   ii) the separated catalysts can be reused in the process for a number of times, and
   iii) also the catalyst is non corrosive, therefore most of the serious problems associated with homogeneous catalyst used in the earlier homogeneous catalyzed processes for the preparation of aralkylated aromatic compounds are overcome in the process of this invention.

2) The process of this invention has also number of advantages over the prior art processes based on the use of solid catalyst for the aralkylation of aromatic compounds, as follows:
   i) The activity of the said catalyst used in the process of present invention is much higher and hence the reaction is much faster and thereby the time required for completing the reaction is much shorter,
   ii) The process of the present invention can be used for aralkyating both small and large size aromatic compounds with both small and large size aralkylating agents to produce the corresponding aralkylated compounds, using said supported solid catalyst containing meso- or macroporous catalyst carrier.
   iii) In the process of this invention, since moisture-free inert gas is bubbled through the reaction mixture continuously, said by-product formed in the reaction is removed continuously and thereby the reverse aralkylation reaction is avoided or minimised, thus requiring shorter time for completing the reaction.
   iv) In the process of this invention, by using pressure higher than 1 atm, it is possible to carry out the aralkylation reaction at a temperature higher than the normal boiling point of either of the reactants and the solvent, and thereby the reaction period for completing the reaction is shortened and/or the inhibition of the reaction due to strong adsorption of the reactants, products or solvent on the catalyst is avoided or minimised,
   v) By the process of this invention, even the aralkylation of benzene, naphthalene or anthracene, which does not contain any aromatic ring activating electron donating group such as alkyl, alkoxy, hydroxy etc. group, at mild reaction conditions is rapid and hence accomplished at shorter reaction periods.
   vi) Moreover, using the supported solid catalyst of this invention, a rapid aralkylation of aromatic compound is possible even when the reaction mixture contains moisture; the catalyst is not deactivated by the presence of moisture in the reaction mixture.

We claim:

1. A supported solid catalyst, containing mixed metal oxides or halides deposited on porous catalyst carriers or support, useful for the Friedel-Crafts reactions, represented by the formula:

$$A_aMZ_b(c)/S$$

wherein, A is selected from chemical elements Ga, Al, Zn, Fe, Ti, Th, Zr or a mixture of two or more thereof; M is selected from chemical elements In, Tl or a mixture thereof;

Z is selected from chemical elements cl, Br or I; S is porous catalyst support or carrier; a is A/M mole ratio in the range of about 0.001 to about 100; b is number of atoms of Z needed to fulfil the valence requirement of the metallic elements $A_aM$ present in the supported catalyst; c is weight percentage loading of $A_aMZ_b$ deposited on said catalyst support or carrier (S) in the range of about 0.5 wt % to about 50 wt %.

2. A supported solid catalyst as claimed in claim 1, wherein S is selected from micro- and/or meso porous zeolites and zeolite-like materials, synthetic and natural clays, silica gel, alumina and mesoporous and macroporous catalyst carriers containing $SiO_2$, $Al_2O_3$, SiC, $ZrO_2$, $HfO_2$ or a mixture thereof.

3. A supported solid catalyst as claimed in claim1, wherein c is from 2 wt % to 20 wt %.

4. A supported solid catalyst as claimed in claim 1, wherein A is chemical element Ga, Fe, Zn or a mixture thereof.

5. A supported solid catalyst as claimed in claim 1, wherein Z is chemical element Cl.

6. A process for the preparation of supported solid catalysts, useful for the Friedel-Crafts reactions, wherein said catalysts are represented by formula:

$$A_aMZ_b(c)/S$$

wherein, A is selected from chemical elements Ga, Al, Fe, Ti, Th, Zr or a mixture of two or more thereof, M is selected from chemical elements In, Tl or a mixture thereof, Z is selected from chemical elements Cl, Br or I; S is porous catalyst support or carrier; a is A/M mole ratio in the range of about 0.001 to about 100; b is number of atoms of Z needed to fulfil the valence requirement of the metallic elements $A_aM$ present in the supported catalyst; c is weight percentage loading of $A_aMZ_b$ deposited on said catalyst support or carrier (S) in the range of about 0.5 wt % to about 50 wt %;

said process comprises:

(i) depositing on said catalyst support mixed metal halides represented by formula:

$$A_aMD_d,$$

wherein A is selected from chemical elements Ga, Al, Zn, Fe, Ti, Th, Zr or a mixture of two or more thereof, M is selected from chemical elements In , Tl or a mixture thereof; D is chemical group selected from halogen Cl, Br or I or a mixture thereof; a is A/M mole ratio in the range of about 0,001 to about 100; and d is number of atoms of D needed to fulfil the valence requirement of the metallic elements $A_aM$; from non-aqueous moisture-free solvent, in which said mixed metal halides are dissolved, by known catalyst impregnating techniques, such that the weight percent loading of said mixed metal halides on said catalyst support is in the range of about 0,5 wt % to about 50 wt %; or depositing on said catalyst support mixed metal compounds represented by formula:

$$A_aME_e,$$

wherein A is selected from chemical elements Ga, Al, Zn, Fe, Ti, Th, Zr or a mixture of two or more thereof; M is selected from chemical elements In, Tl or a mixture thereof; E is chemical group selected from O, $NO_3$, OH, halo, alkoxides or $C_nH_{2n+1}COO$, wherein n is in the range of 0 to 15; a is A/M mole ratio in the range of about 0,001 to about 100; e is number of groups of E needed to fulfil the valence requirement of the metallic elements $A_aM$; by known catalyst impregnation, coating or co-precipitation techniques, such that the weight percent loading of said catalyst support is in the range of about 0. 5 wt % to about 50 wt %, (ii) heating the catalyst mass obtained from the step-i to dryness at a temperature of about 25° C. to about 250° C. under vacuum or in presence of air or inert gas, (iii) calcining the dried mass obtained from step-ii at a temperature of about 100° C. to about 700° C. under vacuum or in presence of air or inert gas for about 0 1 h to about 100 h to get the catalyst.

7. A process as claimed in claim 6, wherein S is selected from micro- and/or meso porous zeolites and zeolite-like materials, synthetic and natural clays, silica gel, alumina and meso porous and macroporous catalyst carriers containing $SiO_2$, $Al_2O_3$, SiC, $ZrO_2$, $HfO_2$ or a mixture thereof.

8. A process as claimed in claim 6, wherein c is from 2 wt % to 20 wt %.

9. A process as claimed in claim 6, wherein the period of catalyst calcination is from 0.25 h to 25 h.

10. A process as claimed in claim 6, wherein A is chemical element Ga, Fe, Zn or a mixture thereof.

11. A process as claimed in claim 6, wherein Z is chemical element Cl.

* * * * *